US00PP20610P3

(12) United States Plant Patent
Lindgren et al.

(10) Patent No.: US PP20,610 P3
(45) Date of Patent: Dec. 22, 2009

(54) ***PENSTEMON* PLANT NAMED 'SWEET JOANNE'**

(50) Latin Name: ***Penstemon* hybrid**
Varietal Denomination: 'Sweet Joanne'

(75) Inventors: Dale T. Lindgren, North Platte, NE (US); Kim A. Todd, Lincoln, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 190 days.

(21) Appl. No.: 11/823,164

(22) Filed: Jun. 27, 2007

(65) Prior Publication Data

US 2008/0127380 P1 May 29, 2008

Related U.S. Application Data

(60) Provisional application No. 60/817,323, filed on Jun. 29, 2006.

(51) Int. Cl.
*A01H 5/00* (2006.01)

(52) U.S. Cl. ..... Plt./465

(58) Field of Classification Search ..... Plt./465
See application file for complete search history.

(56) References Cited

OTHER PUBLICATIONS

Anonymous. Nebraska Release. New Penstemon Called Sweet Joanne. available at ianrnews.unl.edu. Apr. 23, 2008.*

* cited by examiner

*Primary Examiner*—Wendy C. Haas
(74) *Attorney, Agent, or Firm*—McKee, Voorhees & Sease, P.L.C.

(57) ABSTRACT

A new and distinct hybrid of *Penstemon* plant characterized by dark pink flowers with streaks of purple on the lower petals. The plant has a high resistance to insects and is very long lived.

1 Drawing Sheet

Botanical name: The present invention relates to a new *Penstemon* hybrid plant.

Variety denomination: The new plant has the varietal denomination 'Sweet Joanne'.

BACKGROUND OF THE INVENTION

*Penstemon* is a diverse genus of plants with species that occur in each of the states in the United States (except Hawaii), Canada, Mexico and Guatemala. Many selections within species have been made and named. Selections from interspecific hybrids are less common. However, many European hybrids were derived from intercrossing species and hybrids from Mexico with the large flowered *P. cobaea* from the central United States. Most of theses large and colorful flowered European hybrids do not over winter in the United States except in the milder climates.

The present invention relates to a new and distinct cultivar of a *Penstemon* hybrid, made from intersectional crosses between the fasciculus section and the peltanthera section of *Penstemon* which has resulted in a group of plants known as the 'Mexicana' series. Plants in the fasciculus section are found primarily in Mexico. This series displays intermediate characteristics between the parents. In 1980, the first of the 'Mexicali' series was established by introducing the large flowered variety called 'Sensation' into the 'Mexicana' series. The 'Mexicali' series is believed to have received their winter hardiness and long bloom from the *Penstemon* section fasciculus and larger flowers from the *Penstemon* section peltanthera and the variety 'Sensation'.

Seeds of the 'Mexicali' series were distributed to members of the American *Penstemon* Society (APS) through the APS exchange, and the resultant seedlings of some of these 'Mexicali' selections performed well. Two selections from the 'Mexicali' series were made in Colorado and released through the Plant Select® plants program, 'Red Rocks'™ and 'Pikes Peak Purple'™.

SUMMARY OF THE INVENTION

Among the features which distinguish the new variety from other presently available and commercial *Penstemon* cultivars known to the inventors are the following combination of characteristics: its dark pink flowers with streaks of purple on the lower petals, its extreme resistance to pests and its very long life as compared to other *penstemon* selections. The plant has a medium height that is suitable for landscape purposes as either a border or accent plant.

This new cultivar has been reproduced only by asexual propagation (division and tissue culture). Each of the progeny exhibits identical characteristics to the original plant. Asexual propagation by tissue culture using standard micropropagation techniques with terminal and lateral shoots as done in North Platte, Nebr., shows that the foregoing characteristics and distinctions come true to form and are established and transmitted through succeeding propagations. The present invention has not been evaluated under all possible environmental conditions, thus the phenotype may vary with variations in environment without a change in the genotype of the plant.

BRIEF DESCRIPTION OF THE DRAWINGS

The accompanying photographs illustrate specimens of the new cultivar and shows a three-year-old *Penstemon* 'Sweet Joanne' growing in the garden in North Platte, Nebr. depicted in color as nearly correct as it is possible to make in a color illustration of the character.

Figure 1:
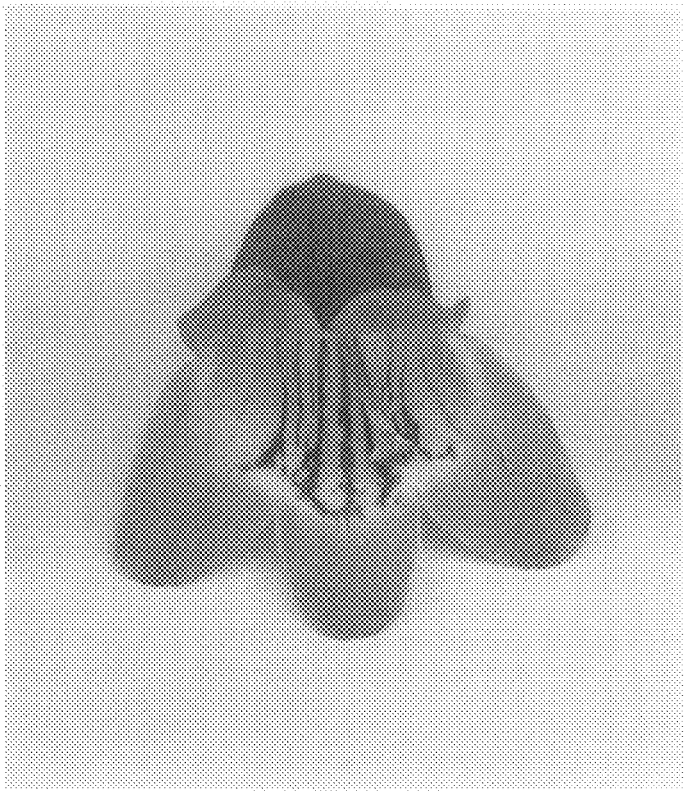
FIG. 1 is a photograph of the 'Sweet Joanne' plant.
Figure 2:
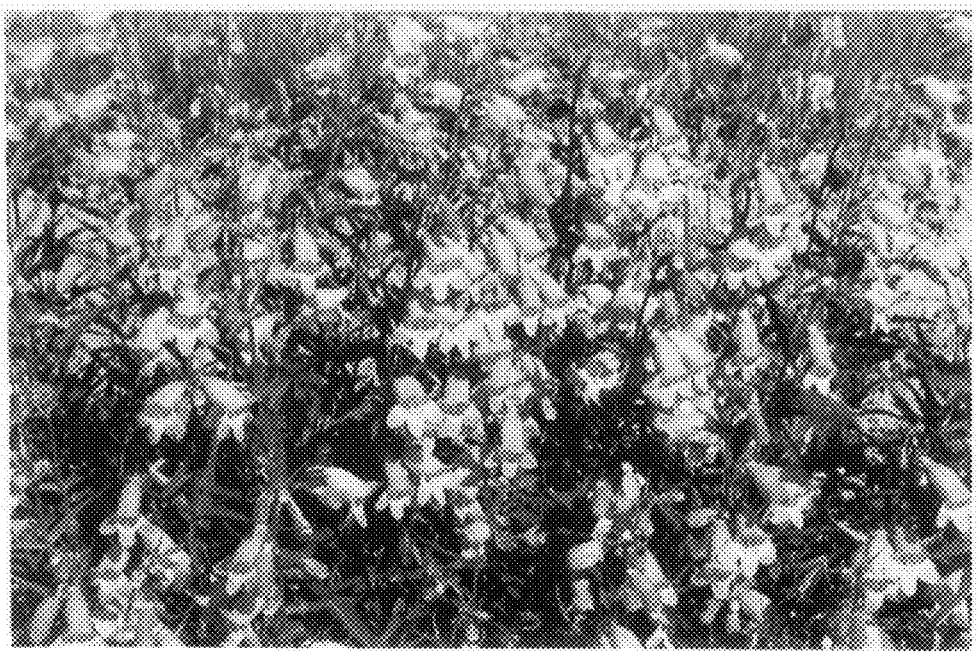
FIG. 2 is a photograph giving a view of the flowers of 'Sweet Joanne' wherein they are of a dark pink/lavender on the outside, while on the inside the flowers are white with streaks of purple/red on the lower inside throat.

Throughout this specification, color references and/or values are based upon the Colour Chart of The Royal Horticultural Society of London, England (1966), except where common terms of color definition are employed.

DESCRIPTION OF THE NEW VARIETY

The following is a detailed description of the new *Penstemon* hybrid based on observations of one to three-year-old specimens grown in the garden in North Platte, Nebr.

Plant:

*Type.*—Herbaceous perennial.

*Form.*—Open leafy fountain of branched stems.

*Hardiness.*—USDA Zone 5 to 9.

*Size.*—2002 51.4 cm and 66 cm wide (1-year old). 2003 56.5 cm and 56 cm wide (2-year-old). 2004 50.0 cm and 54.6 cm wide (3-year-old). *Overall plants averaged 56.5 cm tall and 56.0 cm wide, not including bloom.

*Habit.*—Upright.

*Fascicles.*—Present.

Leaf:

*Type.*—Simple.

*Arrangement.*—Opposite.

*Shape.*—Linear.

*Venation.*—Predominantly parallel.

*Margins.*—Serrate.

*Apex.*—Acute.

*Base.*—Acute to rounded (leaves closest to top more rounded; lower leaves acute).

*Blade size.*—Mature size=7.9 cm long and 0.6 cm wide. Ratio of approximately 13 to 1 (length to width) on older and younger leaves.

*Vestiture.*—Minutely pubescent on surface of leaves and margins of leaves.

*Aspect.*—Glossy.

*Texture.*—Smooth.

*Leaf color.*—Bright green. Between dark yellowish green 141B and moderately green 132B.

Inflorescence:

*Type.*—Thyrse.

*Number of flowers.*—31 to 32 per thyrse.

*Peduncle.*—Height — 12–15 cm. Diameter — 1 to 1.5 mm. Color — Green group 140C. Texture — Smooth.

*Pedicel.*—Length — 0.6 to 0.7 cm. Texture — Smooth. Color — Green group 140C.

*Bloom period.*—May to frost.

Flower bud:

*Size.*—(Flowers buds vary depending upon bud age) Early bud stage — 1.0 cm long and 0.45 cm wide. Medium bud stage — 1.6 cm long and 0.65 cm wide. Late bud stage — 2.2 cm long and 0.8 cm wide.

*Description.*—Closed tubular, bulging.

*Color.*—(Color varies depending upon bud age) Early bud stage — white (White group, 155A) to yellowish white (Green group, 157C). Medium bud stage — white (Green-white group, 157C) at calyx end to pink (Red purple group, 64D) at bud tip. Late bud stage — white at calyx end to dark pink 70B at bud tip.

Flower:

*Type.*—Campanulate.

*Shape.*—Lobe extended bilabiate.

*Size.*—2000 3.3 cm long, 2.3 wide and 2.3 high. 2003 3.74 cm long, 2.57 wide and 2.38 high. 2004 3.35 cm long, 2.50 wide and 2.24 high.

*Color.*—Dark pink/lavender (Purple-violet group, 82B) on the outside, while the tube is white (White Group 155D) with streaks of purple/red (Red-purple group, 63A) on the lower inside throat.

*Stamen number.*—4 fertile, 1 sterile.

*Stamen shape.*—Attached to upper fused petals, curved downward at the tip, ending with two distinct small lobes.

*Stamen size.*—19.5 mm long with thick, golden hairs at the tip, decreasing in intensity toward the back of the flower.

*Anther sacs.*—Opposite, opening across the connection of each stamen.

*Anther size.*—2.5 mm long and 1.0 mm wide for unopened anthers and 1.6 mm long and 1.2 mm wide in opened/dehisced anthers.

*Style size.*—25.5 mm long.

*Calyx size.*—12.35 mm long.

*Calyx color.*—Green group 140C.

*Filaments.*—2.0 to 2.1 mm long. White.

*Pollen color.*—White.

*Pistil.*—2.8 cm long, Yellow white 158D.

*Fragrance.*—None.

*Lastingness.*—As a cut flower, 6 to 10 days approximately.

Fruit:

*Type.*—Capsule.

*Fertility.*—Highly fertile with self and closely related types. Highly infertile with unrelated species.

*Size.*—1.3 cm long and 0.5 cm wide.

*Color.*—Yellow green 154B, changing to brown (Greyed-orange group, 165B) when mature.

Seed:

*Shape.*—Oval.

*Size.*—1.9 mm long and 1.2 mm wide.

*Color.*—Dark brown (Brown group, 200A).

Insect tolerance: Excellent tolerance to pests.

The following description is of one to three year-old plants of the new variety grown outdoors in North Platte, Nebr. for the entire year. The new variety flowers from the end of May to frost. Phenotypic expression may vary with environmental, cultural and climatic conditions, as well as differences in conditions of light and soil.

COMPARISONS TO SIMILAR *PENSTEMON*

The new variety of 'Sweet Joanne' is different from the commercially available 'Red Rocks'™ or 'Pikes Peak Purple'™. 'Sweet Joanne' displays larger flower size, a dark pink flower with streaks of purple on the lower petals and extreme resistance to pests. The plants of 'Sweet Joanne' also form a tighter, upright plant as compared to 'Red Rocks'™ or 'Pikes Peak Purple'™. Further, 'Sweet Joanne' has shown 100% survival over the winter season whereas 'Red Rocks'™ displayed 80% survival and 'Pikes Peak Purple'™ had 60% survival.

I claim:

1. A new and distinct hybrid of *Penstemon* plant substantially as described and illustrated herein.

* * * * *